(12) United States Patent
Yun et al.

(10) Patent No.: US 11,324,794 B2
(45) Date of Patent: May 10, 2022

(54) COMPOSITION FOR PREVENTING, IMPROVING, OR TREATING DECREASE IN INTESTINAL FUNCTION, COMPRISING BAMBOO SHOOT HYDROLYZATE OR FERMENTED BAMBOO SHOOT AS ACTIVE INGREDIENT

(71) Applicant: OZLDNF CO., LTD., Jeollanam-do (KR)

(72) Inventors: Choong-ho Yun, Seoul (KR); Jae Hun Jeong, Gwangju (KR)

(73) Assignee: OZLDNF CO., LTD., Damyang-gun (KR)

( * ) Notice: Subject to any disclaimer, the term of this patent is extended or adjusted under 35 U.S.C. 154(b) by 0 days.

(21) Appl. No.: 16/624,199

(22) PCT Filed: Dec. 5, 2017

(86) PCT No.: PCT/KR2017/014145
§ 371 (c)(1),
(2) Date: Dec. 18, 2019

(87) PCT Pub. No.: WO2018/236011
PCT Pub. Date: Dec. 27, 2018

(65) Prior Publication Data
US 2020/0108114 A1    Apr. 9, 2020

(30) Foreign Application Priority Data
Jun. 19, 2017   (KR) .................. 10-2017-0077491

(51) Int. Cl.
*A61K 36/899* (2006.01)
*A23L 33/105* (2016.01)

(52) U.S. Cl.
CPC .......... *A61K 36/899* (2013.01); *A23L 33/105* (2016.08); *A23V 2200/32* (2013.01); *A61K 2236/19* (2013.01)

(58) Field of Classification Search
None
See application file for complete search history.

(56) References Cited

FOREIGN PATENT DOCUMENTS

| | | |
|---|---|---|
| CN | 101142979 A | 3/2008 |
| CN | 101077197 B | 7/2011 |
| CN | 105410949 A | 3/2016 |
| CN | 106235341 A | 12/2016 |
| CN | 106720440 A | 5/2017 |
| JP | 2007215484 A | 8/2007 |
| KR | 10-2005-0028508 | 3/2005 |
| KR | 10-2011-0034763 | 4/2011 |
| KR | 10-2015-0080871 | 7/2015 |
| KR | 20150080871 A | 7/2015 |
| KR | 10-2016-0076866 | 6/2016 |

OTHER PUBLICATIONS

Chaudhury et al. (2011) J. Scientific and Industrial Res. vol. 70, pp. 199-203. (Year: 2011).*
Singhal et al. (2013) Critical Reviews in Food Science, 53: 517-534. (Year: 2013).*
Chongtham et al. (2011) Comprehensive Reviews in Food Science and Safety, vol. 10: 153-169. (Year: 2011).*
Raskin et al. (2004) Current Pharmaceutical Design, 10: 3419-3429. (Year: 2004).*
Revilla et al. (1998) J. Agric. Food Chem. 46: 4592-4597. (Year: 1998).*
Satya et al. (2010) Trends in Food Science and Technology, 21: 181-190. (Year: 2010).*
Park et al., "Effects of bamboo shoot consumption on lipid profiles and bowel function in healthy young women" Jul. 2009.
Science and Technology of Food Industry, China Academic Journal Electronic Publishing House, vol. 26, No. 7, Jul. 2005 (English Abstract).
ISBN 978-7-5337-7077-8, 2016.
Natural Remedies: Nondrug Healing Strategies That Work Best, ISBN 7-5062-5252-X, 2001.
ISBN 978-7-5067-6582-4, 2013.

* cited by examiner

*Primary Examiner* — Russell G Fiebig
(74) *Attorney, Agent, or Firm* — Maschoff Brennan (57) ABSTRACT

The present invention relates to a composition for preventing, improving or treating intestinal dysfunction, including an enzyme-degraded product of bamboo shoots or a fermented product of bamboo shoots as an active ingredient. Accordingly, the pharmaceutical composition or the food composition of the present invention is effective for preventing or treating intestinal dysfunction such as constipation, etc., and includes a plant-derived component which minimizes adverse effects on the human body.

7 Claims, 3 Drawing Sheets

COMPOSITION FOR PREVENTING, IMPROVING, OR TREATING DECREASE IN INTESTINAL FUNCTION, COMPRISING BAMBOO SHOOT HYDROLYZATE OR FERMENTED BAMBOO SHOOT AS ACTIVE INGREDIENT

TECHNICAL FIELD

The present invention relates to a pharmaceutical composition for preventing or treating intestinal dysfunction and a food composition for preventing intestinal dysfunction or improving intestinal function. More particularly, the present invention relates to a pharmaceutical composition for preventing or treating intestinal dysfunction, which includes an enzyme hydrolysate or fermented product of bamboo shoots, as well as a food composition for preventing intestinal dysfunction or improving intestinal function.

BACKGROUND ART

Patients suffering from discomfort due to various intestinal dysfunctions caused by dietary habits, stress or congenital causes are increasing.

In particular, constipation is known to be the origin of different diseases from old times, is a state of not only having no appetite but also suffering abdominal bloating, and wherein toxins not excreted from the stomach are absorbed into the intestine and thus blood, hence accelerating skin aging and causing headache, acne, skin rash, etc. when constipation is severe, it may cause hemorrhoids including, for example, anal fissures, prolapsed hemorrhoid, etc. In more severe cases, colon cancer may also occur.

Constipation refers to a condition wherein a person defecates less than two times per week and an amount of feces is less than 35 g per week. In fact, lack of exercise or stress accumulation may cause reduction in bowel movement and deterioration in motility of the stomach for excretion, Constipation may simply refer to feces staying in the colon for more than a normal retention time, wherein the feces are usually excreted. 12 to 72 hours after ingestion, however, the type of ingested food affects bowel movement time. That is, a fiber-rich food absorbs fluid from the intestine, increases its volume, is converted into excrement and stimulates excretion, while foods with low fiber contents act in the opposite way from the above functions. Constipation itself is not a disease but may be a symptom. However, gases such as hydrogen sulfide, nitrosoamine, ammonia, phenol, etc, generated by abnormal fermentation in the intestine due to constipation may cause headache, visual disturbance, allergies or the like. Moreover, diverse and serious secondary diseases such as abdominal pain, skin ailment, bad breath, colon disease, arteriosclerosis, hypertension, stroke, immune deficiency and so on may also be caused. Therefore, active prevention and treatment is needed. Among therapies for improvement of constipation and smooth intestinal function, dietary fiber, water intake and exercise have been attempted as basic treatments for all types of constipation. Further, as a drug secondarily used for treatment of constipation, cathartics have only temporary effects and some thereof cause various side effects. In particular, an irritable detersive agent has reduced effects in long-term use and furthermore may lead to destruction of the enteric plexus when administered over a long period, hence losing bowel function.

The most common functional food material for relieving constipation is dietary fiber and various foods including kelp, yacon, *Saururus chinensis*, bamboo shoot tea, *Malva verticiliata* tea, aloe, seaweed, etc. are commercially available, but whether effects thereof have been scientifically proven is uncertain and being questioned.

Various methods have been studied in order to solve the above problems, and it is necessary to study a substance which can help diaphoretic deterioration such as constipation without adverse effects on the human body.

DISCLOSURE

Technical Problem

It is an object the present invention to provide a plant-derived pharmaceutical composition that Is effective for preventing or treating intestinal dysfunction such as constipation and does not cause adverse effects on the human body.

Another object of the present invention is to provide a plant-derived food composition that is of effective for preventing intestinal dysfunction improving intestinal function and does not cause adverse effects in the human body

Technical Solution

According to an aspect of the present invention, there is provided a pharmaceutical composition for preventing or treating intestinal dysfunction, which includes an enzyme-degraded product of bamboo shoots or a fermented product of bamboo shoots as an active ingredient.

The bamboo shoot may be any one of bamboo shoots selected from *Sinoarundinaria nigra, Phyllostachys nigra, Phyllostachys bambusoides, Arundinaria simonii, Sasa borealis* and *Sasa quelpaertensis*.

The bamboo shoots may include at least one of bamboo shoot shells and shell-free contents of bamboo shoots.

The bamboo shoot may be sequentially extracted with water and alcohol to increase the content of insoluble dietary fiber.

The bamboo shoot may be a pulverized product of bamboo shoots or an extract of bamboo shoots.

The enzyme-degraded product of bamboo shoots may be a product of enzymatic degradation by one or more enzymes selected from the group consisting of arabanase, cellulose, glucanase, hemicellulose, amylase, and xylanase.

The bamboo shoot-fermented product may be a fermentation product obtained by inoculating bamboo shoots with *Bacillus subtilis*.

The intestinal dysfunction may be at least one selected from constipation, indigestion, diarrhea, irritable bowel syndrome, abdominal pain and abdominal distension.

According to another aspect of the present invention, there is provided a food composition for preventing intestinal dysfunction or improving intestinal function, which includes an enzyme-degraded product of bamboo shoots or a fermented product of bamboo shoots as an active ingredient.

Advantageous Effects

The pharmaceutical composition of the present invention is effective for preventing or treating intestinal dysfunction such as constipation and can minimize adverse effects on the human body.

Further, the food composition of the present invention is effective for preventing intestinal dysfunction or improving intestinal function, and can minimize adverse effects on the human body.

BEST MODE

The present invention may include various modifications and embodiments, and specific embodiments will be illustrated in the accompanying drawings and concretely described in the detailed description. It is to be understood, however, that the invention is not limited to these specific embodiments but includes all modifications, equivalents and alternatives falling within the spirit and scope of the invention. In the disclosure of the present invention, if it is considered that concrete explanation of relevant known art may make the gist of the present invention ambiguous, detailed description thereof will be omitted.

Hereinafter, the pharmaceutical composition for prevention or treatment of intestinal dysfunction according to the present invention will be described.

The pharmaceutical composition for preventing or treating intestinal dysfunction according to the present invention may be an enzymatic hydrolysate or fermented product of bamboo shoots and, more preferably, an enzymatic hydrolysate of bamboo shoots (referred to as "enzyme-degraded product of bamboo shoots").

The bamboo shoot may be a shoot of bamboo such as *Sinoarundinaria nigra*, *Phyllostachys nigra*, *Phyllostachys bambusoides*, *Arundinaria simonii*, *Sasa borealis* and *Sasa quelpaertensis*. The scope of the present invention is not limited thereto and any kind of bamboo shoots able to exhibit similar effects may be used in the present invention.

The bamboo shoot may be obtained from bamboo shoot shell or shell-free contents of bamboo shoots.

The bamboo shoot is preferably subjected to pretreatment wherein the bamboo shoot is sequentially extracted with water and alcohol to increase a content of insoluble dietary fiber.

Specifically, extraction with water may be performed by immersing bamboo shoot shells or bamboo shoots in water at room temperature for 1 hour to 5 hours and then heating the same at 80 to 100° C. for 30 minutes to 2 hours in order to obtain insoluble dietary fiber. Thereafter, alcohol is added to the insoluble dietary fiber and the mixture is heated at 15 to 70° C. for 1 hour to 5 hours, followed by separating the supernatant to increase the content of the insoluble dietary fiber while removing the water-soluble dietary fiber residue. The higher the content of insoluble dietary fiber, the more effective the improvement of bowel function.

Pretreatment of bamboo shoots is the same as described above, but the scope of the present invention is not limited thereto and conventional hot water extraction or alcohol extraction may also be applied.

The bamboo shoot may be a pulverized product of bamboo shoots or an extract of bamboo shoots.

The bamboo shoot extract includes not only crude extract obtained by treating the pulverized product of bamboo shoots with an extraction solvent but also processed products of the crude extract. For example, the bamboo shoot extract may be prepared in a powder form by an additional process such as vacuum distillation and lyophilization or spray drying. The extract also includes fractions obtained by further fractionating the crude extract.

The bamboo shoot extract is an extract of water, alcohol having 1 to 4 carbon atoms or a mixed solvent thereof, and the extraction method is not particularly limited.

When water is used as the solvent, hot water extraction is preferred. For instance, the extraction may be performed at a temperature of 80 to 105° C., preferably 90 to 100° C. for 0.5 to 24 hours, preferably 1 to 6 hours. Even if no hot water is used as a solvent, bamboo shoot components may be extracted in a diluted solution obtained by diluting bamboo shoot powder with cold water or water at room temperature. When the bamboo shoot component is extracted using cold water or water at room temperature, the extraction may be performed independent of fermentation, or the bamboo shoot component may be eluted during fermentation by inoculating the bamboo shoot with fermentation microorganism.

An extract obtained using an aqueous alcohol solution having 1 to 4 carbon atoms may be used. For instance, extraction is carried out with the aqueous alcohol solution such as ethanol, methanol or isopropanol, preferably 20 to 80% by weight aqueous alcohol solution and, more preferably 50 to 70% by weight aqueous alcohol solution. When alcohol extracts are used, before inoculation with *Bacillus subtilis*, a concentrate having lowered alcohol content obtained by evaporating alcohol portion from the alcohol extract or the alcohol extract pre-treated by concentration and drying may be dissolved in water and used.

In addition, in a wide range of meanings, the bamboo shoot extract may include a diluted solution obtained by diluting bamboo shoots with water.

The enzymatic hydrolysate of bamboo shoots, that is, the enzyme-degraded product of bamboo shoots, may be obtained by enzymatic degradation with enzymes such as arabanase, cellulose, glucanase, hemicellulose, amylase and xylanase. However, the type of enzymes is not limited to those described above and various carbohydrases may be employed.

The bamboo shoot-fermented product may be obtained by inoculation using *Bacillus subtilis*, or fermented according to any conventional fermentation method.

The bamboo shoot-fermented product may be a bamboo shoot solid fermented product or a bamboo shoot liquid fermented product.

The bamboo shoot solid fermented product may be obtained by adding water to milled bamboo shoots and fermenting the same through inoculation with the fermentation microorganisms. An amount of added water is determined such that water content ranges from 15 to 50% by weight, preferably 25 to 40% by weight in order to proceed fermentation while growing the fermentation microorganism. The inoculation may be performed after adding water to achieve the above water content. Otherwise, after adding water to soak the milled bamboo shoots, the soaked bamboo shoots are subjected to inoculation.

The bamboo shoot liquid fermented product may be obtained by inoculating the bamboo shoot extract or the diluted solution thereof with the fermentation microorganism.

In order to enhance the growth of fermentation microorganism before inoculation using the fermentation microorganism in the production of the bamboo shoot solid fermented product or the bamboo shoot liquid fermented product, a nutrient source of the fermentation microorganism such as a protein source, a carbohydrate source, vitamins or an inorganic substance may be further mixed. The nutrient source of the fermentation microorganism may be a commercially available medium or may be added separately only with necessary nutrients.

The milled bamboo shoots, bamboo shoot extract, or a mixture of the same with the fermentation microorganism may be heat-sterilized before inoculation using the fermentation microorganism.

The intestinal dysfunction may include constipation, dyspepsia, diarrhea, irritable bowel syndrome, abdominal pain, abdominal distension, etc. However, the scope of the present invention is not limited thereto and various symptoms or diseases due to intestinal dysfunction may be included.

As used herein, the term " . . . including as an active ingredient" means inclusion of an amount sufficient to achieve desired efficacy or activity of the enzyme-degraded or fermented product of bamboo shoots. In one embodiment of the invention, the enzyme-degraded or fermented product of bamboo shoots in the composition of the present invention may be contained in an amount of at least 0.001 mg/kg, preferably at least 0.1 mg/kg, more preferably at least 10 mg/kg, even more preferably at least 100 mg/kg, even more preferably at least 250 mg/kg, most preferably at least 1000 mg/kg. The enzyme-degraded or fermented product of bamboo shoots is a natural substance and does not adversely affect the human body even when administered in an excessive amount. Therefore, the quantitative upper limit of the enzyme-degraded or fermented product of bamboo shoots contained in the composition of the present invention may be selected by persons skilled in the art ("those skilled in the art") within a suitable range.

The pharmaceutical composition of the present invention may be prepared using any pharmaceutically acceptable and physiologically acceptable adjuvant in addition to the above-mentioned active ingredients. Examples of the adjuvant may include excipients, disintegrants, sweeteners, binders, coating agents, swelling agents, lubricants or flavoring agents.

The pharmaceutical composition may be processed into a pharmaceutical formulation containing at least one pharmaceutically acceptable carrier in addition to the above-described active ingredients for administration.

The pharmaceutical formulation may have a form such as a granule, a powder, a tablet, a coated tablet, a capsule, a suppository, a liquid, a syrup, a juice, a suspension, an emulsion, a drip agent or an injectable liquid agent. For example, in order to formulate the composition into tablets or capsules, the active ingredient may be combined with an oral and non-toxic pharmaceutically acceptable and inactive carrier such as ethanol, glycerol, water, and the like. Also, if desired or necessary, suitable binders, lubricants, disintegrants and coloring agents or a mixture thereof may also be included. Suitable binders include, but are not limited to, natural sugars such as starch, gelatin, glucose or beta-lactose, natural and synthetic gums such as corn sweeteners, acacia, tragacanth or sodium oleate, sodium stearate, magnesium stearate, sodium benzoate, sodium acetate, sodium chloride, and the like. Disintegrants include, but are not limited to, starch, methyl cellulose, agar, bentonite, xanthan gum and the like.

Acceptable pharmaceutical carriers for a composition to be formulated into a liquid solution may include saline, sterile water, Ringer's solution, buffered saline, albumin injectable solution, dextrose solution, maltodextrin solution, glycerol, ethanol and a mixture of at least one among the above components, which are biocompatible and suitable for sterilization. If necessary, other conventional additives such as an antioxidant, a buffer and a bacteriostatic agent may be added. In addition, diluents, dispersants, surfactants, binders and lubricants may be further added to formulate the composition into injectable formulations such as aqueous solutions, suspensions, emulsions, etc., pills, capsules, granules or tablets.

The pharmaceutical composition of the present invention may be administered orally or parenterally. In case of parenteral administration, the administration may be carried out by intravenous injection, subcutaneous injection, muscle injection, intraperitoneal injection, transdermal administration, etc. Preferably, oral administration is applied.

An appropriate dosage of the pharmaceutical composition according to the present invention may depend on factors such as formulation method, administration method, age, body weight, gender, pathological conditions, diet, administration time, administration route, excretion rate and responsiveness of the patient, and a skilled physician may readily determine and prescribe a dosage effective for desired treatment or prophylaxis. According to a preferred embodiment of the present invention, the daily dosage of the pharmaceutical composition of the present invention may range from 0.001 to 10 g/kg.

The pharmaceutical composition of the present invention may be prepared in a unit dose form by formulation using a pharmaceutically acceptable carrier and/or excipient according to any method easily executed by those skilled in the art to which the present invention pertains, or introduced into a multi-dose container to produce a final product. In this case, the formulation may be in the form of solutions, suspensions or emulsions in oils or aqueous media, or in the form of excipients, powders, granules, tablets or capsules, and may additionally contain a dispersing or stabilizing agent.

The present invention also provides a food composition for preventing intestinal dysfunction or improving intestinal function, which includes an enzymatic hydrolysate (or enzyme-degraded product) or fermented product of bamboo shoots as an active ingredient.

The description of the food composition is the same as the description of the pharmaceutical composition for prevention or treatment of intestinal dysfunction according to the present invention described above.

The food composition according to the present invention may be used as a functional food or added to various foods. Foods to which the composition of the present invention is added may include, for example, beverages, alcoholic beverages, confectionery, diet bars, dairy products, meats, chocolates, pizza, breads, noodles, gums, ice creams, vitamin complexes, health supplements, etc.

The food composition of the present invention may contain, as an active ingredient, an enzyme-degraded or fermented product of bamboo shoots, as well as a component that is typically added in the course of food production. For example, proteins, carbohydrates, fats, nutrients, seasonings, flavoring agents or the like may be included. Examples of the above-mentioned carbohydrates may include: monosaccharides such as glucose, fructose, etc.; disaccharides such as maltose, sucrose, or oligosaccharides, etc.; polysaccharides, for example, typical sugars such as dextrin, cyclodextrin, etc., and sugar alcohols such as xylitol, sorbitol, erythritol, etc. The flavoring agents used herein may include natural flavoring agents [thaumatin, *stevia* extracts (for example, rebaudioside A, glycyrrhizin, etc.)] and synthetic flavoring agents (saccharine, aspartame, etc.). For instance, when the food composition of the present invention is manufactured as a drink or a beverage, citric acid, liquid fructose, sugar, glucose, acetic acid, malic acid, juice and/or other plant extracts may further be included in addition to the enzyme-degraded or fermented product of bamboo shoots.

The present invention provides a health functional food that includes a food composition for improving or preventing intestinal dysfunction, which includes an enzyme-degraded or fermented product of bamboo shoots as an active ingredient. The health functional food refers to a food prepared by adding the enzyme-degraded or fermented product of bamboo shoots to a food material such as beverage, tea, spice, gum or confection, or formulated into encapsulated, powdered or suspended products, which bring specific effects in health by intake of the food. However, unlike the conventional medicine, the health functional food has the advantage that, since real food is used as a raw material, there are no adverse effects possibly occurring when a drug is taken for a long time. The health functional food of the present invention thus obtained is very useful because the food can be ingested routinely. An amount of the enzyme-degraded or fermented product of bamboo shoots in such a health functional food may vary depending upon types of the health functional food to which the product is added, and thus cannot be uniformly determined, however, may be added within a range that does not deteriorate the original taste of the food. Usually, the amount ranges from 0.01 to 50% by weight ('wt. %'), preferably 0.1 to 20 wt. %. Further, in case of health functional food in the form of pills, granules, tablets or capsules, this may be usually added in an amount of 0.1 to 100 wt. %, preferably 0.5 to 80 wt. %. In one embodiment, the health functional food of the present invention may be in the form of a pill, tablet, capsule or beverage.

PREFERRED EMBODIMENT OF INVENTION

Example

Preparation of Bamboo Shoot

In June 2015, *Sinoarundinaria nigra* (S) collected in Damyang-gun was boiled entirely at 100° C. or more for hour and then stored in cold water for separation of bamboo shoots and shells, followed by quick freezing and storing the same at −80° C. Frozen bamboo shoot shells and bamboo shoots were lyophilized, uniformly to a size of 100 mesh and used while keeping in cold storage. Analysis of the sample was repeated three times, and the average value thereof was determined.

Pretreatment Step

Figure 6:
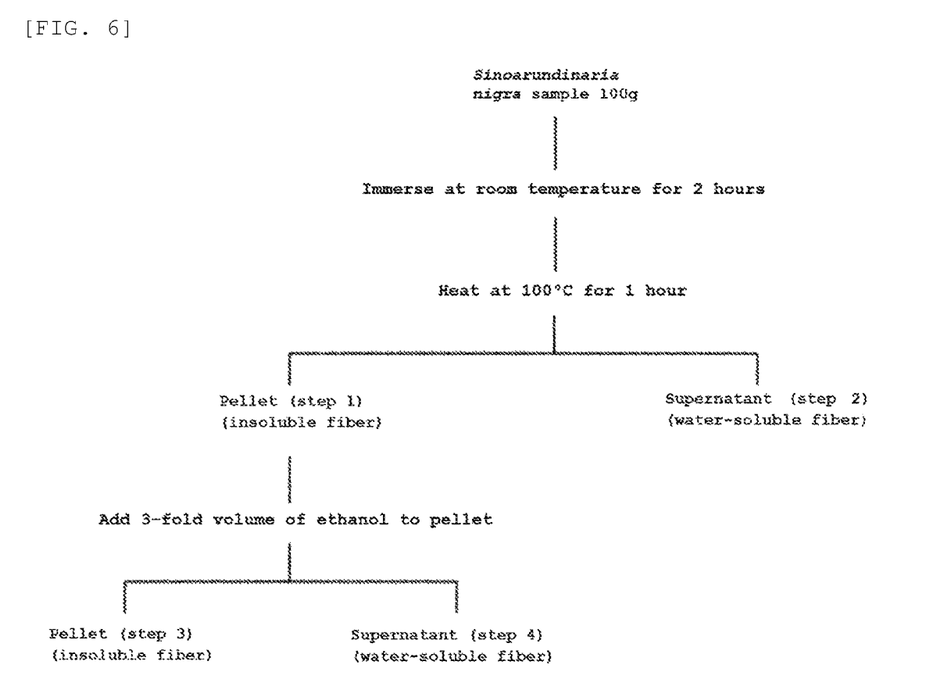
FIG. 6 is a flow diagram illustrating the pretreatment process in the embodiment of the present invention.

Bamboo shoots and bamboo shoot shells were extracted using water and ethanol as extraction solvents, respectively. The extraction methods and conditions are shown below. Distilled water was added to 100 g of the *Sinoardundinaria nigra* (S) sample obtained according to the above method, and the sample was immersed at room temperature for 2 hours and then heated at 100° C. for 1 hour. In this step, pelletized bamboo shoot dietary fibers which are insoluble fibers were obtained (step 1) except for water-soluble fibers as the supernatant (step 2). Then, 3-fold volume of ethanol was added to the pelletized bamboo shoot fibers, and the mixture was left at 5° C. for 2 hours to obtain pelletized insoluble bamboo shoot fibers (step 3) except the water-soluble fibers as the supernatant (step 4). The fractions of bamboo shoots obtained separately from the above steps were collected and used as experimental samples. The enzyme degraded product of bamboo shoots were prepared using the samples obtained in step 3 which had the highest content of insoluble dietary fibers. A flow diagram of the pretreatment process is shown in FIG. 6.

Example 1: Preparation of Enzyme-Degraded Product of Bamboo Shoots

Enzymatic degradation was performed using the insoluble dietary fiber fraction (step 3) in bamboo shoot powder obtained according to the above method. That is, 10 ml of the fraction was added to 300 ml of a 50 mM sodium acetate buffer having pH 5.0, and the mixture was swollen at 180 rpm for 1 hour in a shaking incubator at 50° C. Then, 0.5% Viscozyme, 0.5% Celluclast and 0.5% Fungamyl were added, followed by enzymatic degradation at 180 rpm and the same temperature for 0, 3, 6, 12 and 24 hours. After completion of the enzyme reaction, the enzyme was inactivated by heating at 90° C. for 5 minutes. The enzyme-degraded product was dried using a lyophilzer and the prepared powder was stored in a refrigerator at 4° C.

Example 2: Preparation of Enzyme-Degraded Product of Bamboo Shoot Shells

An enzyme-degraded product was prepared in the same manner as in Example 1 except that the bamboo shoot shell powder obtained according to the above method was used instead of the bamboo shoot powder.

Example 3: Preparation of Fermented Product of Bamboo Shoots

Bamboo shoot (*Sinoardundinaria niqra* (S)) shells and bamboo shoots were separated and washed thoroughly. A bamboo shoot sample except for shells was cut to a size of 3 to 4 cm and used. 1.5 kg of bamboo shoots, *Bacillus subtilis,* 900 g of raw sugar and 450 ml of fresh water were placed in a glass container, followed by fermentation in a fermentation chamber at 30° C. and 15% relative humidity, thereby preparing the fermented product of bamboo shoots.

Example 4: Preparation of Fermented Product of Bamboo Shoot Shells

A fermented product of bamboo shoot shells was prepared in the same manner as in Example 3, except that bamboo shoot shells were used instead of bamboo shoots.

Analysis of Dietary Fiber of Bamboo Shoots

Results of bamboo shoot dietary fiber analysis to extraction steps according to the extraction process of bamboo shoot fiber are shown in Table 1 below. At this time, an amount of bamboo shoot dietary fibers (water soluble dietary fiber+insoluble dietary fiber) was measured according to a static method.

TABLE 1

| Extraction step | Total dietary fiber (g/dry weight of 100 g) | |
| --- | --- | --- |
| | Bamboo shoot | Bamboo shoot shell |
| Step 1 | 1.76 ± 0.43 | 1.84 ± 0.45 |
| Step 2 | 32.98 ± 2.35 | 54.24 ± 2.45 |
| Step 3 | 30.50 ± 2.20 | 49.28 ± 2.25 |
| Step 4 | 2.44 ± 0.75 | 4.64 ± 0.76 |

Measurement of Dietary Fiber Yield Enzyme Degradation Time

A total amount of dietary fibers to enzymatic degradation time of the enzyme-degraded product prepared according to Examples 1 and 2, respectively, was measured by the above method and measured results thereof are shown in Table 2 below.

TABLE 2

| Enzymatic degradation time (h) | Total dietary fiber (5/dry weight of 100 g) (increase rate, %) | |
| --- | --- | --- |
| | Bamboo shoot | Bamboo shoot shell |
| 0 | 26.78 ± 2.35 (100) | 45.14 ± 4.22 (100) |
| 3 | 30.64 ± 2.87 (114) | 49.32 ± 2.74 (109) |
| 6 | 34.44 ± 2.86 (129) | 54.57 ± 3.25 (121) |
| 12 | 37.74 ± 2.23 (141) | 58.33 ± 2.68 (129) |
| 24 | 38.70 ± 2.62 (145) | 62.04 ± 2.42 (137) |

Experimental Example

Laboratory Animals and Breeding Conditions

Laboratory mice under the following conditions were used.

Genealogy and Species: Sprague Dawley (SD) rat
Source: Samtaco Co., Ltd.
Number of purchased animals and gender: Male
Age (week) of purchased animals and weight range: 6 weeks, 190 to 220
Number of animals (male) at the time of administration: 49
Age (week) of animals and weight range at the time of administration: 7 weeks, 210 to 240 g.

After purchasing the animals, the animals were quarantined and acclimated in an animal breeding room environment for 7 days to observe general health status, and then, healthy ones were selected and used for test.

Individual identification was indicated on each individual number tag by an oil-soluble magic pen. The breeding box was identified by affixing the identification card wherein the test serial number, the name of test substance, test items, the date of acquisition, the period of acclimation, the date of group separation, the test period, the gender/animal number and the person in charge of the test are written.

Except for the subjects with abnormality occurred and the subjects without normal increase in weight during acclimation, the remaining subjects were divided into groups such that the average weight and standard deviation between the groups were uniformed. Each treatment section was divided into seven (7) groups wherein each group includes 7 subjects and these subjects were separately bred.

Test environments in the animal breeding room were set as follows: temperature of 22±3° C.; relative humidity of 50±20%; rate of ventilation (10 to 15) times/hr; illumination period of 12 hours (between 8:00 and 20:00); and intensity of illumination ranging from 150 to 300 Lux, wherein the animals were bred with feed and drinking water, and were isolated during acclimation and experiment.

During acclimation and experiment, each of the subjects was separately bred in a plastic breeding box [270(W) 500(D)×200(H) mm] within a clean breeding room.

The feed was a rat feed for laboratory animals (laboratory rat feed, 38057, Purina Korea), and the drinking water was freely provided.

Organization of Test Groups and Administration of Test Substance

The test groups were organized as summarized in Table 3 below.

TABLE 3

| Test group | Test substance (daily dosage) | Administration method |
| --- | --- | --- |
| Con | D.W | Oral |
| Lop | Loperamide (4 mg/kg) | Oral |
| Bis | Loperamide (4 mg/kg) + Bisacodyl (4 mg/kg) | Oral |
| 1-100 | Loperamide (4 mg/kg) + Example 1 (100 mg/kg) | Oral |
| 1-200 | Loperamide (4 mg/kg) + Example 1 (200 mg/kg) | Oral |
| 2-100 | Loperamide (4 mg/kg) + Example 2 (100 mg/kg) | Oral |
| 2-200 | Loperamide (4 mg/kg) + Example 2 (200 mg/kg) | Oral |
| 3-200 | Loperamide (4 mg/kg) + Example 3 (200 mg/kg) | Oral |
| 4-200 | Loperamide (4 mg/kg) + Example 4 (200 mg/kg) | Oral |

After one week of acclimation, the test substance, that is, ioperamide as a conventional constipation inductive material, bisacodyl as a conventional constipation therapeutic agent, the enzyme-degraded products in Examples 1 and 2 (fermented for 24 hours) and the fermented products in Examples 3 and 4, respectively, were repeatedly administered in the stomach once a day for a total of 7 days by means of a syringe for oral administration (Sonde). Except for the control group (Con), all test groups were subjected to administration of loperamide (4 mg/kg) in order to induce constipation.

Bisacodyl is a stimulant laxative and a therapeutic agent mostly used for treatment of constipation. This agent stimulates the colon to induce peristalsis of the colon and help bowel movement, and is substantially not absorbed in the intestine but defecated. Further, this agent may stimulate the peripheries of sensory nerves cause parasympathetic nerve reflex, leading to peristalsis of the colon. In addition, local axon reflex and segmental reflex may also occur to widely spread the peristaltic motion of the colon.

Statistical Processing

The test results were expressed as mean±standard deviation. Statistical significance of a difference between the groups was determined by the Student t test method. It was considered to be statistically significant when p value is less than 0.05 (p<0.05).

Experimental Example 1: Measurement of Body Weight, Dietary Intake and Amount of Drinking Water The body weight was measured twice a week on the day before the experiment when group separation was conducted, and twice a week on the day after administration, respectively. The experimental dietary intake was measured by feeding 100 g of test diet at a predetermined time and, after 24 hours, the remaining amount was measured to determine the dietary intake. The drinking water was fed by 250 ml at a predetermined time and the remaining water was measured on the next day to determine a total amount of the water intake.

During the test period, body weight change, dietary intake and water intake were summarized in Tables 4 and 3 below. There were no substantial differences in body weight, change and water intake for 7 days between the control group (Con) and other test substances.

TABLE 4

| Test group | Body weight (g) | | Body weight change (g) |
|---|---|---|---|
| | Before test (A) | After test (B) | (B) − (A) |
| Con | 205.20 ± 3.30 | 285.42 ± 4.76 | 80.22 ± 3.37 |
| Lop | 205.13 ± 2.45 | 278.58 ± 6.82 | 73.45 ± 5.48 |
| Bis | 205.06 ± 2.30 | 274.54 ± 4.23 | 69.49 ± 4.73 |
| 1-100 | 204.63 ± 2.35 | 285.81 ± 4.53 | 80.46 ± 5.21 |
| 1-200 | 204.93 ± 2.00 | 285.93 ± 3.63 | 81.01 ± 3.67 |
| 2-100 | 205.03 ± 2.31 | 277.05 ± 3.76 | 72.02 ± 2.11 |
| 2-200 | 204.93 ± 2.29 | 275.64 ± 3.74 | 70.71 ± 4.43 |
| 3-200 | 205.03 ± 2.31 | 283.08 ± 3.76 | 78.05 ± 3.21 |
| 4-200 | 204.93 ± 2.29 | 284.63 ± 3.74 | 79.70 ± 4.83 |

TABLE 5

| Test group | Dietary intake (g) | Water intake (g) |
|---|---|---|
| Con | 24.40 ± 0.63 | 31.04 ± 0.84 |
| Lop | 22.10 ± 0.79 | 31.66 ± 0.09 |
| Bis | 22.92 ± 0.91 | 31.19 ± 1.24 |
| 1-100 | 24.44 ± 1.11 | 29.74 ± 1.28 |
| 1-200 | 22.96 ± 0.66 | 30.03 ± 2.45 |
| 2-100 | 21.00 ± 0.59 | 29.93 ± 1.08 |
| 2-200 | 21.87 ± 0.60 | 30.43 ± 1.89 |
| 3-200 | 23.04 ± 0.25 | 28.70 ± 1.26 |
| 4-200 | 23.96 ± 0.63 | 30.53 ± 2.40 |

Experimental Example 2: Measurement of Number of Feces and Feces Weight Change

The feces were sampled daily and the number and weight of the feces were measured. Further, the sampled feces were dried in a drier at 70° C. for 24 hours.

Figure 1:
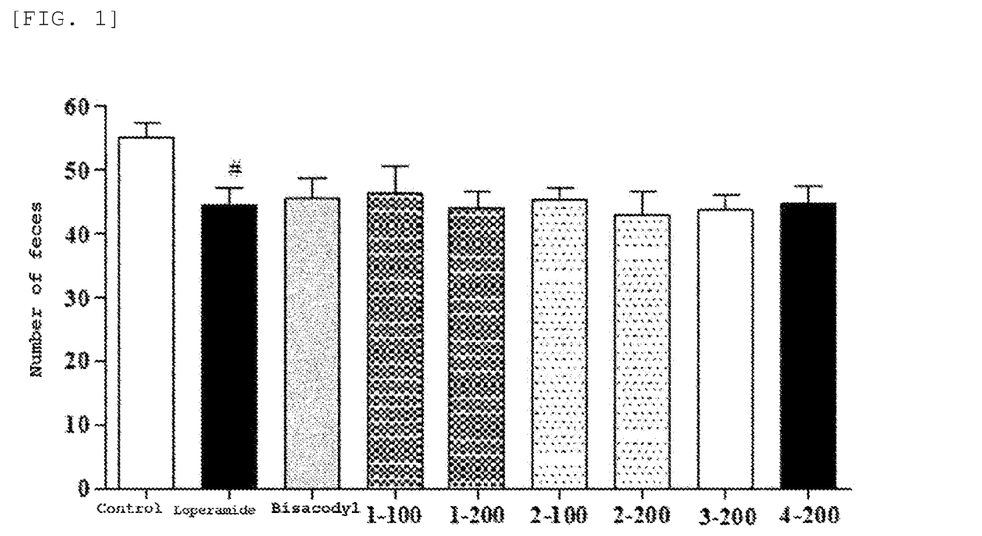
FIG. 1 illustrates results of measurement of the number of feces according to Experimental Example 2.

FIG. 1 shows the results of counting the number of feces on the 7$^{th}$ day after induction of constipation. According to the results, the number of feces was significantly decreased in Lop group (44.40±2.54), as compared to Con group (55.14±2.06), thereby indicating induction of constipation (P<0.05). There was no significant change between Lop group and other test substance groups.

Figure 2:
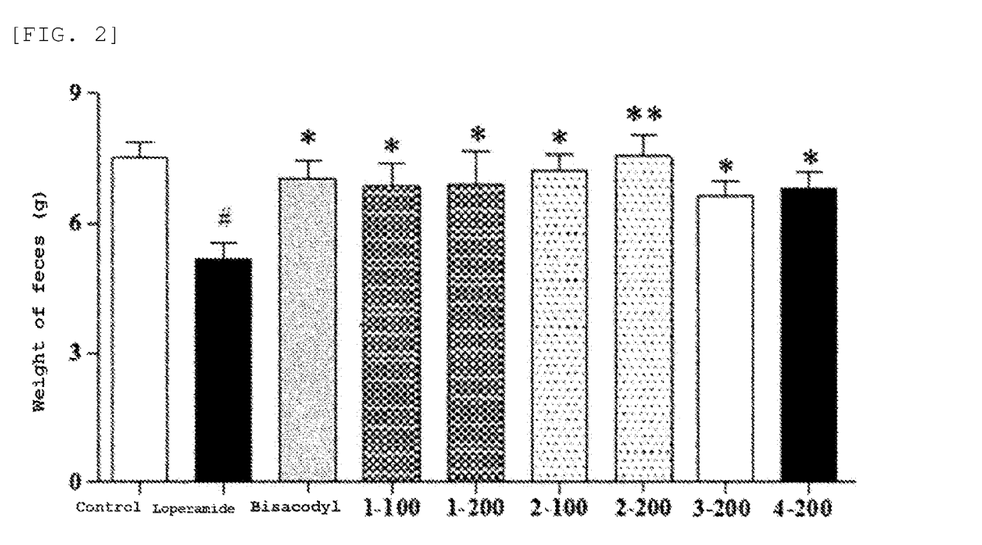
FIG. 2 illustrates results of measurement of the weight of feces according to Experimental. Example 2.

Further, FIG. 2 shows results of counting the number of feces and measuring the weight of feces in the test groups. According to the results, as compared to Con group (7.52±0.30 g), Lop group (5.02±0.36 g) showed a significant decrease in weight (P<0.05). Further, as compared to Lop group, Bis group (6.82±0.35 g), 1-100 group (6.70±0.45 g), 1-200 group (6.75±0.45 g), 2-100 group (6.93±0.32 g), 2-200 group (7.54±0.43 g), 3-200 group (6.62±0.33 g) and 4-200 group (6.69±0.34 g) showed a significant increase in weight (P<0.05).

In addition, 3-200 group and 4-200 group, which are administration groups of the fermented products prepared according to the fermentation method, showed relatively smaller weights of the feces, compared to 1-200 group and 2-200 groups which are administration groups of the enzyme-degraded products, thereby demonstrating that the enzyme-based hydrolysates of bamboo shoots may be relatively effective for constipation rather than the fermented product of bamboo shoots.

Experimental Example 3: Measurement of Water Content of Feces

The feces were sampled daily and the number and weight of the feces were measured. Further, the sampled feces were dried in a drier at 70° C. for 24 hours. A percentage of water content was calculated by subtracting the weight after drying from the weight before drying to estimate the water content and converting the estimated value as the percentage to a total weight of the feces.

Figure 3:
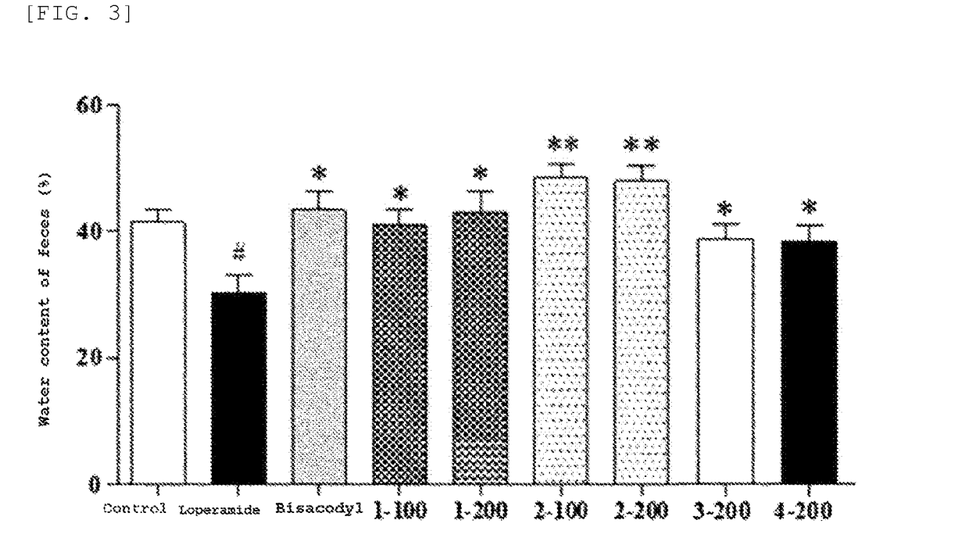
FIG. 3 illustrates results of measurement of water content in the feces according to Experimental Example 3.

FIG. 3 shows the results of measuring the water content of the feces. As shown in the figure, Bis group (44.02±1.34%), 1-100 group (41.01±2.35%), 1-200 group (42.62±2.05%), 2-100 group (48.49±2.09%), 2-200 group (47.97±2.29%), 3-200 group (38.80±1.75%) and 4-200 group (37.8±2.04%) illustrated a significant increase in water content, as compared to Con group (29.98±1.89%). Specifically, for 2-100 group and 2-200 group, the water content of the feces was the most greatly increased (P<0.05).

Further, for 3-200 group and 4-200 group as the fermented product administration groups, the water content of feces was measured to be relatively lower than that in 1-200 group and 2-200 group as the administration group of the enzyme-degraded products, thereby demonstrating that the enzyme-based hydrolysates of bamboo shoots may be relatively effective for constipation rather than the fermented product of bamboo shoots.

Experimental Example 4: Analysis of Influence on Digestive Tract Migration Rate

After fasting a laboratory animal for 15 hours on the 7th day of constipation induction, a 0.5 ml suspension including 10% Arabic gum (Sigma, USA) and 5% activated charcoal (Sigma, USA) was orally administered to the animal. 30 minutes later, the animal was sacrificed, the gastrointestinal tract was removed, and a migration rate was calculated by dividing a length wherein green colored feces are excreted among the intestinal tract length between the duodenum and the rectum, with passage of time. Activated carbon used in the present experiment was prepared by burning various organic substances, which has high adsorption, non-toxicity and no pharmacological effects.

Figure 4:
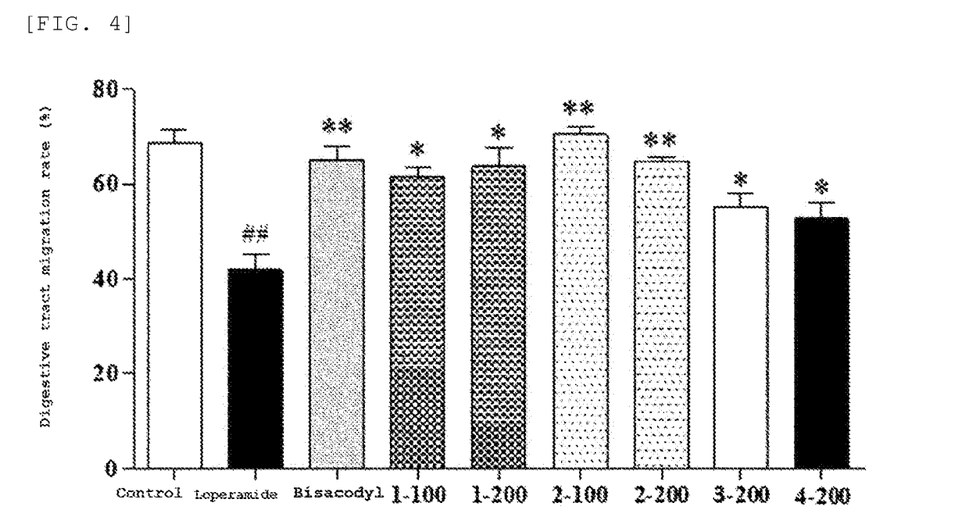
FIG. 4 illustrates analyzed results of influence on migration rate in the digestive tract according to Experimental Example 4.

The results of the experiment with respect to influence of test substances on digestive tract migration rate are shown in FIG. 4. According to the results, a significant decrease in effects was observed in Lop group (42.10±3.49%) compared to Con group (68.63±2.72%) (P<0.01). As compared to the administration group of loperamide alone, all of Bis group (65.02±2.86%), 1-100 group (61.64±1.51%), 1-200 group (63.69±4.22%), 2-100 group (70.45±1.79%), 2-200 group (64.61±0.91%), 3-200 group (56.62±2.25%) and 4-200 group (53.05±1.89%) showed a significant increase in effects (P<0.05, P<0.01).

In addition, for the fermented product administration groups, that is, 3-200 group and 4-200 group, the digestive tract migration rate was measured to be relatively low, compared to the enzyme-degraded product administration groups, that is, 1-200 group and 2-200 group, thereby demonstrating that the enzyme-based hydrolysates of bamboo shoots may be relatively more effective for constipation rather than the fermented product of bamboo shoots.

Experimental Example 5: Counting Number of Intestinal Stools

The number of intestinal stools was counted by scarifying a laboratory rat on the 8th day after administration of loperamide and observing the number of feces remaining in the colon tract.

Figure 5:
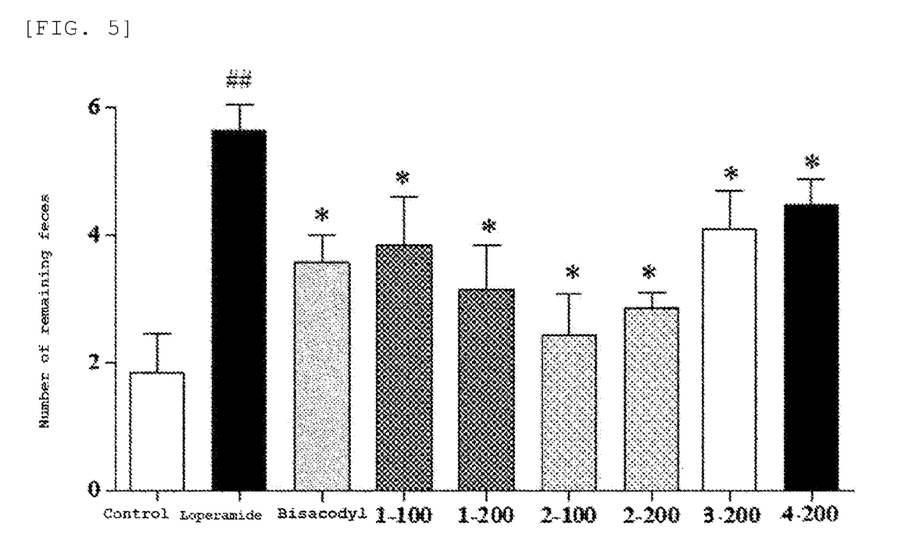
FIG. 5 illustrates results of the number of intestinal stools according to Experimental Example 5.

On the last day of the experiment, all laboratory animals were sacrificed and the number of feces remaining in the rectal region was measured. The measured results are shown in FIG. 5. According to the results, the number of feces was significantly increased in Lop group (5.66±0.63), as compared to Con group (1.86±0.55). Further, as compared to Lop group, all of Bis group (3.62±0.86), 1-100 group (3.89±0.64), 1-200 group (3.23±0.68), 2-100 group (2.47±0.65), 2-200 group (2.91±0.24), 3-200 group (4.09±0.32) and 4-200 group (4.50±0.26), respectively, showed significant results, thereby demonstrating decrease in number of feces remaining in the intestinal tract ($P<0.05$).

In addition, for the fermented product administration groups, that is, 3-200 group and 4-200 group, the number of feces remaining in the intestinal tract was counted to be relatively larger as compared to the enzyme-degraded product administration groups, that is, 1-200 group and 2-200 group, thereby demonstrating that the enzyme-based hydrolysates of bamboo shoots may be relatively more effective for constipation rather than the fermented product of bamboo shoots.

As such, although the present invention has been particularly illustrated and described with reference to exemplary embodiments thereof, it will be appreciated by those skilled in the art that many modifications and changes may be possible by supplement, alteration, deletion or addition of constituents without departing from the spirit and scope of the invention as defined in the appended claims, and may also be within the scope of the present invention.

INDUSTRIAL APPLICABILITY

The pharmaceutical composition of the present invention is effective for preventing or treating intestinal dysfunction, while minimizing adverse effects on the human body.

Further, the food composition of the present invention is effective for preventing intestinal dysfunction or improving intestinal function, while minimizing adverse effects on the human body.

The invention claimed is:

1. A pharmaceutical composition for treating constipation, comprising an enzyme-degraded product of bamboo shoots or a fermented product of bamboo shoots as an active ingredient,
   wherein an enzymatic hydrolysate of bamboo shoots or fermented product of the bamboo shoots are obtained from the bamboo shoots,
   wherein the bamboo shoots are subjected to pretreatment wherein the bamboo shoots are sequentially extracted with water and alcohol,
   wherein extraction with water may be performed by immersing the bamboo shoots in water at room temperature for 1 hour to 5 hours and then heating the same at 80 to 100° C. for 30 minutes to 2 hours in order to obtain insoluble dietary fiber,
   wherein alcohol is added to the insoluble dietary fiber and the mixture is heated at 15 to 70° C. for 1 hour to 5 hours, followed by separating the supernatant to increase a content of the insoluble dietary fiber,
   wherein the enzyme-degraded product of bamboo shoots is a product of enzymatic degradation by one or more enzymes selected from the group consisting of arabanase, cellulose, glucanase, hemicellulose, amylase and xylanase,
   wherein the bamboo shoot-fermented product is a fermentation product obtained by inoculating bamboo shoots with *Bacillus subtilis*.

2. The composition according to claim 1, wherein the bamboo shoot is any one of bamboo shoots selected from *Sinoarundinaria nigra, Phyllostachys nigra, Phyllostachys bambusoides, Arundinaria simonii, Sasa borealis* and *Sasa quelpaertensis*.

3. The composition according to claim 1, wherein the bamboo shoot includes at least one of bamboo shoot shells and shell-free contents of bamboo shoots.

4. The composition according to claim 1, wherein the bamboo shoot is sequentially extracted with water and alcohol to increase a content of insoluble dietary fibers.

5. The composition according to claim 1, wherein the enzyme-degraded product of bamboo shoots is a product of enzymatic degradation by one or more enzymes selected from the group consisting of arabanase, cellulose, glucanase, hemicellulose, amylase and xylanase.

6. The composition according to claim 1, wherein the intestinal dysfunction is at least one selected from constipation, indigestion, diarrhea, irritable bowel syndrome, abdominal pain and abdominal distension.

7. A food composition for improving constipation, comprising an enzyme-degraded product of bamboo shoots or a fermented product of bamboo shoots as an active ingredient,
   wherein an enzymatic hydrolysate of bamboo shoots or fermented product of the bamboo shoots are obtained from the bamboo shoots,
   wherein the bamboo shoots are subjected to pretreatment wherein the bamboo shoots are sequentially extracted with water and alcohol,
   wherein extraction with water may be performed by immersing the bamboo shoots in water at room temperature for 1 hour to 5 hours and then heating the same at 80 to 100° C. for 30 minutes to 2 hours in order to obtain insoluble dietary fiber,
   wherein alcohol is added to the insoluble dietary fiber and the mixture is heated at 15 to 70° C. for 1 hour to 5 hours, followed by separating the supernatant to increase a content of the insoluble dietary fiber,
   wherein the enzyme-degraded product of bamboo shoots is a product of enzymatic degradation by one or more enzymes selected from the group consisting of arabanase, cellulose, glucanase, hemicellulose, amylase and xylanase,
   wherein the bamboo shoot-fermented product is a fermentation product obtained by inoculating bamboo shoots with *Bacillus subtilis*.

* * * * *